US005788968A

United States Patent [19]

Weiner et al.

[11] Patent Number: 5,788,968
[45] Date of Patent: *Aug. 4, 1998

[54] METHODS AND COMPOSITIONS FOR SUPPRESSING ALLOGRAFT REJECTION IN MAMMALS

[75] Inventors: Howard L. Weiner, Brookline; David Allen Hafler, West Newton; Charles B. Carpenter, Weston; Mohamed Sayegh, Brookline; Zhengyi Zhang, Malden, all of Mass.

[73] Assignee: AutoImmune, Inc., Lexington, Mass.

[*] Notice: The term of this patent shall not extend beyond the expiration date of Pat. No. 5,593,698.

[21] Appl. No.: 461,661

[22] Filed: Jun. 5, 1995

Related U.S. Application Data

[63] Continuation of Ser. No. 159,044, Nov. 29, 1993, Pat. No. 5,681,556, which is a continuation of Ser. No. 989,884, Dec. 10, 1992, abandoned, which is a continuation of Ser. No. 607,826, Oct. 31, 1990, abandoned.

[51] Int. Cl.$^6$ .................... A61K 39/00; A61K 39/38; C07K 1/00; C07K 14/00
[52] U.S. Cl. .................... 424/184.1; 424/185.1; 530/350
[58] Field of Search .................... 424/184.1; 530/350

[56] References Cited

U.S. PATENT DOCUMENTS 5,130,297  7/1992  Sharma et al. .

FOREIGN PATENT DOCUMENTS

US91/08143  5/1992  WIPO .
US93/03708  10/1993  WIPO .

OTHER PUBLICATIONS

Hancock, W.W. et al., *Transplantation* 55:1112–8, 1993.
Sayegh, M.H. et al., *American Society of Histocompatability and Immunogenics*, 18th Annual Meeting, Abstract, Oct. 1992.
Sayegh, M.H. et al., *American Society of Nephrology*, 25th Annual Meeting, Abstract, Nov. 1992.
Sayegh, M.H. et al., *Proc. Nat'l. Acad. Sci. (u.S.A.)* 89: 7762–9, 1992.
Sayegh, M.H. et al., *Transplantation* 53:162–6, 1992.
Wood et al., *Transplantation* 39(1):56–61, 1985.
Tilney, et al., *J. Immunology* 121(14):1480–1482, 1978.
Milton et al., *J. Exp. Med.* 161:98–112, 1985.
*Remington's Pharmaceutical Sciences*, 1633–1634, 1658–59, 1664–65, 1694–95, 1948.
Mason D.W. et al., *Ann. Rev. Immunol.* 4:119–145, 1986.
Mowat et al., *Immunol. Today* 8(3):93–98, 1987.
Chao et al., *Immunogenetics* 29:231–234, 1989.
Krensky et al., *New Engl. J. Med.* 32:510–517, 1990.
Wood, et al. 1985, Transplantation 39(1): 56–61.
Richman, et al. 1978, Journal of Immunology 140(2): 2429–2434.
Higgins, et al. 1988, Journal of Immunology 140(2): 440–445.
Newman, 1984, Therapeutic Aerosols, Clarke and Davis eds. Aerosols and The Lung 197–224.

*Primary Examiner*—Lynette F. Smith
*Attorney, Agent, or Firm*—Darby & Darby

[57] ABSTRACT

Disclosed herein are methods for suppressing allograft rejection in mammals comprising administering to a mammal about to undergo or having undergone allograft surgery an agent selected from the group consisting of splenic tissue from an allograft donor, splenic extracts, cultured lymphocytes from an allograft donor, extracts of said cultured lymphocytes, MHC antigens, transplantation rejection suppressive fragments and analogs of MHC antigens in an oral or aerosol form. Also disclosed herein are pharmaceutical formulations and dosage forms for use in said methods.

6 Claims, 6 Drawing Sheets

METHODS AND COMPOSITIONS FOR SUPPRESSING ALLOGRAFT REJECTION IN MAMMALS

This is a continuation of application Ser. No. 08/159,044 filed Nov. 29, 1993 (now U.S. Pat. No. 5,681,556), which is a continuation of application Ser. No. 07/989,884 filed Dec. 10, 1992 now abandoned, in turn a continuation of Ser. No. 07/607,826 filed Oct. 31, 1990 now abandoned.

FIELD OF THE INVENTION

This invention relates to methods and compositions for suppressing the immune response in animals. More particularly, but not by way of limitation, the present invention is directed to pharmaceutical formulations and methods for suppressing add controlling the immune response of mammals against the introduction of foreign tissue. The invention also includes methods for prolonging the survival of transplanted organs and tissues.

BACKGROUND OF THE INVENTION

The success of surgical transplantation of organs and tissue is largely dependent on the ability of the clinician to modulate the immune response of the transplant recipient. Specifically the immunological response directed against the transplanted foreign tissue must be controlled if the tissue is to survive and function. Currently, skin, kidney, liver, pancreas and heart are the major organs or tissues with which allogeneic transplantations are performed. It has long been known that the normally functioning immune system of the transplant recipient recognizes the transplanted organ as "non-self" tissue and thereafter mounts an immune response to the presence of the transplanted organ. Left unchecked, the immune response will generate a plurality of cells and proteins that will ultimately result in the loss of biological functioning or the death of the transplanted organ.

Tissue and organ transplant recipients are customarily treated with one or more cytotoxic agents in an effort to suppress the transplant recipient's immune response against the transplanted organ or tissue. For example, cyclosporin (cyclosporin A), a cyclic polypeptide consisting of 11 amino acid residues and produced by the fungus species Tolypocladium inflatum Gams, is currently the drug of choice for administration to the recipients of allogeneic kidney, liver, pancreas and heart (i.e., wherein donor and recipient are of the same species of mammals) transplants. However, administration of cyclosporine is not without drawbacks as the drug can cause kidney and liver toxicity as well as hypertension. Moreover, use of cyclosporin can lead to malignancies (such as lymphoma) and lead to opportunistic infection due to the "global" nature of the immunosuppression it induces in patients receiving long term treatment with the drug, i.e., the hosts normal protective immune response to pathogenic microorganisms is downregulated thereby increasing the risk of infections caused by these agents.

Preliminary results have shown FK-506 (which has a similar mode of action as cyclosporine) to be as potent as cyclosporin in its immunosuppressive qualities and to have fewer toxic side effects than cyclosporin. However, because studies on FK-506 are only in the early stages, it is not available to the general population. Hence, the use of this agent is limited.

Other drugs and/or therapies which are currently administered (either in conjunction with cyclosporin or alone) to suppress the rejection of allogeneic grafts or allografts are also non-specific immunosuppressive drugs or therapies. Steroids, such as prednisone and methylprednisalone, and Azathioprine (an analog of 6-mercaptopurine) are among the non-specific immunosuppressive drugs used to prolong allograft survival in transplantation recipients.

OKT3 monoclonal antibodies, directed against the CD3 antigen present on T-cells, have also been employed as non-specific immunosuppressive therapeutic agents in allograft recipients. However, OKT3 monoclonal antibodies are of murine origin and the patients to whom such monoclonal antibodies are given mount an immune response against these foreign proteins. Thus the usefulness of such materials is limited.

Another drawback to the above-mentioned drugs and antibodies is that they must be administered indefinitely to suppress allogeneic graft rejection, and tolerance to the foreign tissue does not develop.

Total lymphoid irradiation (TLI) is yet another form of non-specific immunosuppressive therapy that has been used clinically and experimentally to prolong allograft survival. The radiation exposure and treatment schedule for TLI were developed for the treatment of Hodgkin's disease and were subsequently found to be immunosuppressive. Although, TLI induces production of the "global" immunosuppression mentioned above and has the same limitations of other global immunosuppressive therapies, it is the only form of immunosuppression currently in use which appears to induce a specific tolerance to allogeneic tissue. However, TLI is cumbersome to administer and is in an early stage of development, and thus its usefulness is limited.

The oral and aerosol administration of antigens has also been recognized as an effective way to suppress the immune response in mammals to these antigens. The advantages of administering antigens via the oral route include: the simplicity of the techniques involved; the convenience of such techniques since many of the methods can be developed in-situ at the research or treatment facility; the safe, non-toxic effects of the ingestion route; and the specificity that can be provided with the antigens.

Recent studies on several autoimmune disease models have demonstrated that the oral administration of antigens can suppress at least the portion of the immune response that is directed against autoantigens and also protect the treated animals from the induction of specific autoimmune diseases. For example, various animal models are available for the study of Type 1 diabetes as an autoimmune disorder. These include the BB rat (Nakbookda, A. F., et al., *Diabetologia* 14: 199–207, 1978) and the NOD (non-obese diabetic) mouse in which diabetes develops spontaneously (Prochazka et al. *Science* 237:286, 1987). Islet-cell specific, CD4- and CD8-positive T-lymphocytes have been implicated as the causative agents responsible for damage to islet beta cells, as demonstrated by transfer of lymphocytes from affected adults to newborn animals (*J. Exp. Med.* 16–823, 1987).

Experimental allergic encephalomyelitis (EAE) is an induced T-cell mediated autoimmune disease directed against myelin basic protein (MBP) that is widely used as an animal model for the human disease Multiple Sclerosis (MS). EAE can be induced in small mammals by intravenous administration of MBP and a strong adjuvant, such as Freund's complete adjuvant. This treatment induces an acute, monophasic autoimmune disease with the characteristics of MS.

Weiner et al., U.S. patent application Ser. No. 07/595,468 entitled Method Of Treating Or Preventing Type 1 Diabetes By Oral Administration Of Insulin, filed Oct. 10, 1990 now abandoned, discloses oral and aerosol compositions and pharmaceutical formulations containing insulin which are useful for treating mammals suffering from or at risk for autoimmune diseases having the characteristics of Type 1 diabetes.

Weiner et al., U.S. patent application Ser. No. 460,852 filed Feb. 21, 1990 now abandoned, (the national stage of PCT Application No. PCT/US88/02139, filed Jun. 24, 1988), which is a continuation-in-part application of U.S. patent application Ser. No. 065,734 filed Jun. 24, 1987 now abandoned, generally discloses the treatment of autoimmune diseases by oral administration of autoantigens.

Weiner et al., U.S. patent appplication Ser. No. 454,806 filed Dec. 20, 1989 now abandoned, discloses the aerosol administration of autoantigens, disease-suppressive fragments of said autoantigens and analogs thereof as an effective method for treating T-cell mediated autoimmune diseases.

Weiner et al., U.S. patent application Ser. No. 487,732, filed Mar. 2, 1990 now abandoned, discloses synergists (enhancers) for use with oral administration of autoantigens, disease suppressive fragments and analogs thereof as effective treatments for T-cell mediated autoimmune diseases.

Weiner et al., U.S. patent application Ser. No. 551,632 filed Jul. 10, 1990 now abandoned, a continuation-in-part of U.S. patent application Ser. No. 379,778, filed Jul. 14, 1989 now abandoned, discloses methods of preventing or treating uveoretinitis in mammals by oral administration of purified S antigen, Interphotoreceptor Retinoid Binding Protein (IRBP) antigen or disease suppressive fragments thereof.

Nagler-Anderson, et al., (Proc. Natl. Acad. Sci. (USA) 83: 7443–7446, 1986), describe the oral administration of collagen to suppress collagen-induced arthritis in a mouse model.

However, the above-mentioned references do not disclose the use of antigens to suppress the mammalian graft rejection mechanism because it has not been shown that the principle of oral administration of transplantation antigens could prevent allograft rejection.

The present invention proposes the clinical administration to mammalian graft recipients of alloantigens via oral and aerosol routes to induce a tolerance to foreign tissue grafts. The invention will be primarily useful in the field of organ transplantation including bone marrow. Although previous studies have shown that alloantigens injected intravenously to recipients can prolong the survival of renal transplants (Transplantation 39:56, 1985; J. Immunol. 121:1480, 1978; J. Exp. Med. 149:1042, 1979), no disclosure or suggestion of introducing these antigens orally or in an aerosol form was made therein.

It is, therefore, an object of the present invention to provide agents and methods for suppressing the detrimental immune response in mammals to the grafting or transplantation of foreign (or "non-self") tissues and organs.

Another object of the present invention is to provide pharmaceutical formulations and-preparations that may be administered to mammals to suppress the immune rejection of surgically transplanted tissues.

A still further object of the invention is to provide synthetic compositions and pharmaceutical formulations that may be administrated to mammals via the oral or aerosol route to suppress the mammalian immune response to the presence of transplanted tissue or organs.

These and other objects of the present invention will become apparent to those of ordinary skill in the art in light of the following.

SUMMARY OF THE INVENTION

It has now been unexpectedly discovered that compositions comprising specific antigenic agents, including by way of non-limiting example allogeneic spleen tissue and cultured lymphocytes and specific Major Histocompatibility Complex (MHC) antigens can be administered to mammals via the oral or aerosol route to suppress the mammalian immune response to surgically transplanted "non-self" organs or tissues. Because the effect is dependent upon-MHC molecules present on the surface of spleen cells, which differ between the tissue donor and the recipient, administration of these antigens alone is expected to be effective.

Orally administered allogeneic splenocytes can suppress the immune response of a host mammal which normally occurs shortly after transplant surgery against surgically transplanted "non-self" tissue in an antigen-specific manner. It has also been found that oral ingestion of allogeneic spleen tissue preparations depresses the delayed type hypersensitivity reaction and mixed lymphocyte reaction in mammals. Compositions and pharmaceutical formulations for oral administration of allogeneic splenocytes may be prepared from natural allogeneic tissue. For administration to humans such compositions comprise synthetic derivatives of antigens i.e., peptide fragments of MHC antigens.

In practicing the method of the present invention, pharmaceutical formulations containing synthetic antigens or natural allogeneic splenic or lymphocyte tissue or cell derivatives are prepared and orally administered to mammalian subjects some time prior to organ or tissue transplant surgery.

Additionally, an aerosol delivery system can be prepared with essentially the dosages of splenocyte derivatives or MHC antigens as above and a pharmaceutically suitable carrier or diluent. The aerosol formulations can also be administered sometime prior to transplant surgery via the aerosol route. These and other improvements will be described in the following descriptions, drawings and appended claims.

BRIEF DESCRIPTION-OF THE DRAWINGS

DETAILED DESCRIPTION OF THE INVENTION

Figure 1:
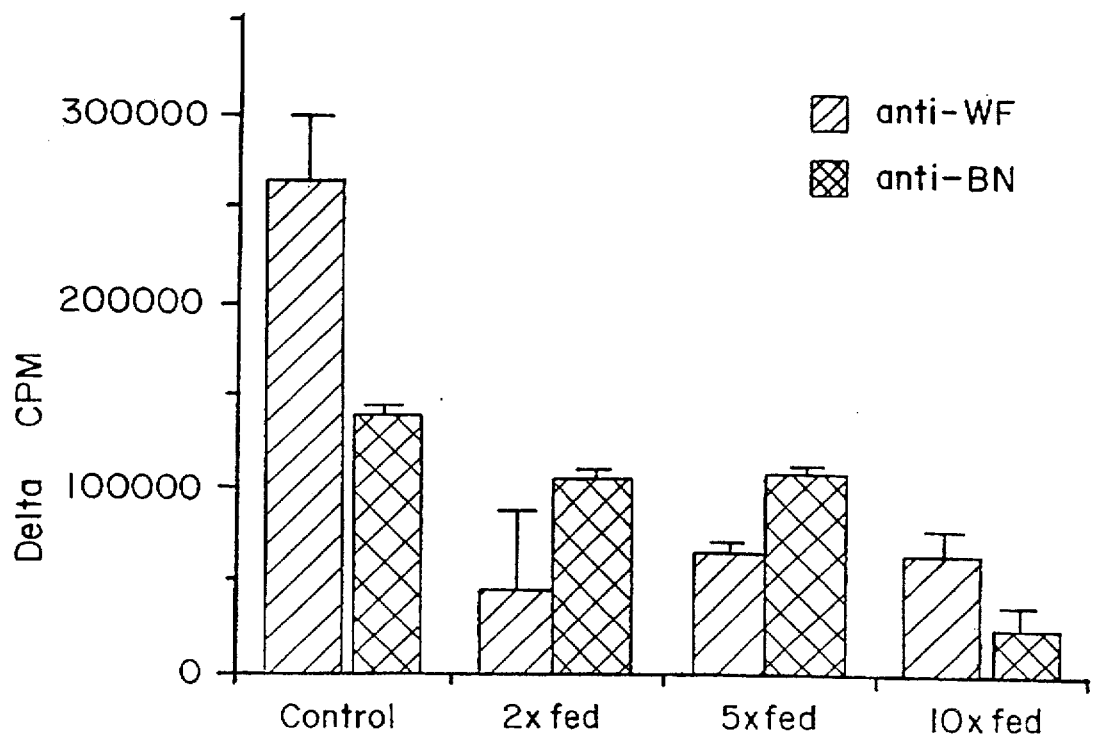
FIG. 1 is a graph showing the effect of feeding allogeneic splenocytes on the mixed lymphocyte reaction (MLR).

The contents of all patent applications, patents and literature references referred to in this specification are hereby incorporated by reference in their entirety.

The present invention addresses the need for an alternate to existing methods for suppressing the immune response directed-against foreign tissue transplants, as for example, post-transplant surgery. In addition, the methods of the present invention provide for prolonged survival of organ and tissue allogeneic grafts (i.e. transplants from individuals of the same species) in a mammal in need of such treatment.

Thus, the present invention provides means whereby the rejection of tissue allografts can be prevented, thus prolonging the survival of transplanted tissue and organs.

It has now been unexpectedly discovered that oral administration of allogeneic splenocytes or synthetic MHC antigens (or immune suppressive fragments or analogs thereof) is effective for suppressing the in vitro mixed lymphocyte reaction which is a model system for the graft rejection response in post-transplant mammalian recipients.

Without wishing to be bound to any particular theory of operation or mechanism of action for the invention it is believed that the oral administration of allogeneic splenocytes or derivatives of MHC antigens pursuant to the present invention affects the immunological mechanisms of graft rejection, i.e. the activation of helper T-cells is decreased by the induction of specific suppressor T-cells.

In the following discussions the following terms shall have the meaning ascribed to them below.

"Oral administration" shall mean both oral administration and enteral administration (delivery directly into the stomach).

"Mammal" shall mean any organism having an immune system and therefore susceptible to allogeneic graft rejection.

"Aerosol" refers to finely divided solid or liquid particles that may be created using a pressurized system such as a nebulizer. The liquid or solid source material contains MHC antigens and/or disease suppressive fragments and analogs thereof as defined herein.

The "aerosol route" of administration means delivery of an aerosol formulation to a host via the nasal or oral airway.

"Major Histocompatibility Complex" (MHC) is defined as a complex series of mammalian cell surface proteins. The MHC plays a central role in many aspects of immunity both in presenting histocompatibility (or transplantation) antigens and in regulating the immune response against conventional (foreign) antigens. There are two types of MHC protein molecules, Class I and Class II. Class I MHC proteins are present on virtually all tissues and Class II MHC proteins are present on the surface of activated T-cells, macrophages and other immune system cells. The human MHC genes (the HLA genetic locus) are located on human chromosome 6, the mouse MHC genes are located in the H-2 genetic locus on mouse chromosome 17 the analogous rat MHC genes are referred to as RTI.

"Class I MHC antigens" are defined as membrane glycoproteins present on the surface of all nucleated cells and play a key role in antigen recognition by CD8+ cytotoxic T-cells.

"Class II MHC molecules" are membrane glycoproteins that form part of the MHC and are most important in the initiation of immune responses. Class II MHC molecules are found mainly on cells of the immune system including B-cells, macrophages, brain astrocytes, epidermal Langerhan's cells, dendritic cells, thymic epithelium and helper T-cells. Class II MHC molecules are involved in regulating the immune response during tissue graft rejection, stimulation of antibody production, graft-versus-host reactions and in the recognition of "self" (or autologous) antigens, among other phenomena.

"MHC antigens" are defined herein as Class I and/or Class II MHC antigens. MHC antigens of the present invention include both Class I and Class II, either alone or in combination.

"Allogeneic tissue extracts" are defined as splenocyte, splenic tissue or cultured lymphocyte extracts obtained from an allogeneic transplant donor and prepared as described below.

"Immune suppressive fragments" means any peptide or polypeptide containing partial amino acid sequences or moieties of analogs of the relevant MHC antigens possessing the ability to induce suppression of the hosts immune response against organ or tissue allogeneic grafts. Such fragments need not possess the alloantigeneic properties of the entire MHC molecule.

"Analogs" of immune suppressive fragments refers to compounds that are structurally related to suppressive fragments of MHC antigens thereof which possess the same biologic activity, i.e., the ability to suppress a mammalian hosts response against a transplanted organ or tissue. The term includes peptides having amino acid sequences which differ from the amino acid sequence of the relevant MHC antigens of the potential graft recipient by one or more amino acid residues.

Disease suppressive fragments and analogs for use in the present invention can be synthesized using well known solid phase synthesis techniques (Merrifield, R. B. *Fed. Proc. Am. Soc. Ex. Biol.* 21: 412, 1962 and *J. Am. Chem. Soc.* 85: 2149, 1963; Mitchel, A. R. et al., *J. Am. Chem. Soc.* 98: 7357, 1976; Tam, J. et al., *J. Am. Chem. Soc.* 105: 6442, 1983). Analogs can be constructed by identifying an equivalent amino acid sequence and using the peptide synthesis techniques disclosed above.

Analogs can be provided-using the known amino acid sequence of MHC antigens as disclosed in *Immunogenetics* 29:231-234, 1989.

Disease-suppressive analogs and fragments can also be obtained using recombinant DNA techniques that are well-known in the art.

Disease suppressive fragments of MHC antigens and analogs thereof can be identified using routine experimentation using suitable in vivo systems such as those of Examples 1-4 below.

T-lymphocytes can be obtained from a potential allograft donor using methods well kown in the art and cultured as described in *Transplantation* 41:549, 1986 and *Transplantation* 48:639, 1989 and administered to a mammal about to undergo or having undergone (as described below) an organ or tissue allograft.

Extracts (or lysates) of splenic tissue or cultured lymphocytes can be prepared using techniques well known in the art such as those described in Example 1 below.

In accordance with the present invention, conventional tissue typing, well-known in the art and routinely conducted on all transplant donors and recipients, is performed on a potential transplant donor to determine the MEC phenotype of the donor tissue or organ. Synthetic MHC antigens, disease suppressive fragments or their analogs can then be synthesized using the techniques described above. These antigens and/or fragments may be administered to mammals, especially humans, who are to receive a transplant, or to patients that have already received transplanted "non-self" tissue. The methods and compositions of the present invention may be used to treat mammals that have previously received "non-self" organ or tissue transplants and are beginning to display the initial symptoms of allograft rejection (such as fever, tenderness of the transplanted organ or loss of function thereof). The method and compositions of the invention are useful to preserve the organ or tissue and damp down or shut off that portion of the immune response of the recipient that is directed against the transplanted tissue or organ. To be effective the compositions and methods of the present invention must be administered before total rejection occurs.

Pursuant to the present invention, MHC antigens or transplantation rejection suppressive fragments or their analogs are ingested by a mammal that is to receive, or has already received a "non-self" organ or tissue transplant via the oral or enteral route, in an amount of between about 0.1 mg per kg body weight and about 10 mg per kg of body weight per day. The pharmaceutical compositions of the invention may be administered as a single dose or in multiple dose form via the oral or enteral route. Preferably, the is administered in an amount between about 1 mg and about 5 mg per kg body weight of said mammal per day. The exact amount to be administered will vary depending on the severity and stage of a patient's disease and the physical condition of the patient.

When administering splenic cells, cultured lymphocytes or extracts thereof, between about $10^6$ and about $10^9$ cell equivalents per kg body weight per day may be administered in single or divided doses.

The timing of such treatments shall be such that, if possible, the pharmaceutical formulations or dosage forms of the present invention are administered between about 7 and about 14 days before the transplantation is performed. The treatment is preferably continued for at least about 6 months after the transplanted organ or tissue has been introduced into the host (recipient) organism and may be continued indefinately if necessary or desirable.

In addition, if a transplant recipient (either already receiving the compositions of the invention or not) begins to manifest symptoms of rejection, the pharmaceutical formulations of the present invention may be administered in increased amounts and/or frequency.

The present invention also is directed to oral dosage forms and pharmaceutical formulations for administration to mammals in order to prolong the survival of or suppress the rejection of a transplanted organ or tissue. It will be understood that any statistically significant prolongation in graft survival pursuant to the treatment of the present invention is within the scope of the invention.

The oral pharmaceutical formulations of the present invention may also contain inert constituents including pharmaceutically acceptable carriers, diluents, fillers, solubilizing or emulsifying agents and salts of the type that are well-known in the art. For example, tablets and caplets may be formulated in accordance with conventional procedures employing solid carriers, such as starch and bentonite, that are well-known in the art. Examples of solid carriers include bentonite, silica, dextrose and other commonly used carriers. Further non-limiting examples of carriers and diluents which may be used in the formulations of the present invention include saline and any physiologically buffered saline solution such as phosphate buffered saline, pH 7–8 and water.

Capsules employed in the present invention may be made from any pharmaceutically acceptable material such as gelatin or cellulose derivatives. The active biological materials of the invention may be administered in the form of sustained release oral delivery systems and/or enteric coated oral dosage forms such as those described in U.S. Pat. No. 4,704,292 issued Nov. 3, 1987, U.S. Pat. No. 4,309,404 issued Jan. 5, 1982 and U.S. Pat. No. 4,309,406 issued Jan. 5, 1982.

It will be appreciated that the unit content of active ingredient or ingredients contained in an individual dose of each dosage form need not in itself constitute an effective amount for suppressing graft rejection since the necessary effective amount can be reached by administration of a plurality of dosage units.

The preferred route of administration of the dosage forms of the present invention is orally or enterally. Preferred oral or enteral pharmaceutical formulations or dosage forms may comprise for example, between about 70 mg and about 500 mg of MHC antigens, disease suppressive fragments or analogs thereof or between about $10^7$–$10^{10}$ cell equivalents when using allogenic cells or extracts thereof.

In an alternative embodiment of the present invention the pharmaceutical formulations of the present invention are administered to mammals in aerosol form. It is anticipated that smaller quantities of the allogeneic tissue extracts or MHC antigens, disease suppressive fragments or their analogs will be required to achieve suppression of graft rejection when using the aerosol form of administration. This has been found to be the case in treating experimental allergic encephalomyelitis (EAE) with myelin basic protein (MBP), and also in treating adjuvant arthritis with collagen as disclosed in the co-pending U.S. patent application of Weiner et al. Ser. No. 454,806 filed Dec. 20, 1989 now abandoned. The quantity of MHC antigens, disease suppressive fragments or the analogs of such materials which may be administered in an aerosol dosage form would be between about 0.01 mg and 10 mg per kg body weight of a mammal per day. The aerosol dosage forms of the present invention may be administered to a patent via the aerosol route in a single dosage form or multiple dosage forms. The exact amount to be administered will vary depending on the state and severity of a patient's disease, the activity of the patients immune system and the physical condition of the patient.

When administering splenic cells, cultured lymphocytes or extracts thereof, between about $10^5$ and about $10^9$ cell equivalents per kg body weight per day may be administered in single or divided doses in an aerosol form.

The aerosol pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the aerosol pharmaceutical formulations of the present invention include water, normal saline and physiologically-acceptable buffered saline solutions such as phosphate buffered saline solutions, pH 7.0–8.0.

Examples of useful solubilizing and emulsifying agents are physiologically balanced salt solutions, phosphate buffered saline and isotonic saline. The salts that may be employed in preparing the aerosol dosage forms of the invention include the pharmaceutically acceptable salts of sodium and potassium.

The route of administration of allogeneic spleen cells, cultured lymphocytes extracts thereof or MHC antigen or disease suppressive fragments or their analogs according to this alternate embodiment of the present invention is in an aerosol or inhaled form. The aerosol compositions of the present invention can be administered as a dry powder or in an aqueous solution. Preferred aerosol pharmaceutical formulations may comprise, for example, a physiologically-acceptable buffered saline solution containing between about 7 mg and about 700 mg of the compositions of the present invention, disease suppressive fragments or analogs thereof.

Dry aerosol in the form of finely divided solid particles of tissue extracts from spleen cells, MHC antigens disease suppressive fragments or analogs thereof that are not dissolved or suspended in a liquid are also useful in the practice of the present invention. The compositions of the present invention may be in the form of dusting powders and comprise finely divided particles having an average particle size of between about 1 and 5 microns, preferably between 2 and 3 microns. Finely divided particles may be prepared by pulverization and screen filtration using conventional techniques that are well known to those skilled in the art. The particles may be administered by inhaling a predetermined quantity of the finely divided material, which can be in the form of a dry atomized powder.

The pharmaceutical formulations of the present invention may be administered via the aerosol route by means of a nebulizer, as an example those described in U.S. Pat. Nos. 4,624,251 issued Nov. 25, 1986; 3,703,173 issued Nov. 21, 1972; 3,561,444 issued Feb. 9, 1971 and 4,635,627 issued Jan. 13, 1971. The aerosol material is inhaled by the subject to be treated.

Other systems of aerosol delivery, including for example the pressurized metered dose inhaler (MDI) and the dry powder inhaler as disclosed in Newman, S. P. in *Aerosols and the Lung*, Clarke, S. W. and Davia, D. eds. pp. 197–224, Butterworths, London, England, 1984 can be used in conjunction with the method of the present invention.

Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.).

In accordance with the present invention, experiments were performed in which the effects of oral administration of allogeneic splenocytes to Lewis rats were studied, with particular attention being given to the effects on the immune response of the transplant recipient. To this end, the in vitro mixed lymphocyte response (MLR), the delayed type hypersensitivity (DTH) reaction, and the in vivo accelerated cardiac allograft rejection techniques were utilized. In each case, the oral administration (to the recipient of a "non-self" tissue transplant) of splenocyte cells from a donor animal resulted in suppression of these T-cell mediated immune reactions. As T-cells have been implicated as the major mediators of allograft rejection, the results of these tests establish the practical efficacy of the methods and pharmaceutical formulations of the present invention.

The present invention is illustrated in specific working examples presented below which are intended to illustrate the present invention without limiting the scope thereof.

EXAMPLE 1: PREPARATION OF MATERIALS AND TEST SUBJECTS

1. Subject Mammals

The test population was comprised of male rats of the Lewis (LEW), Wistar Furth (WF) and Brown Norway (BN) variety (obtained from Harlan Sprague Dawley Inc., Indianapolis, Ind.). The rats in the experiments described below were approximately 8–10 weeks old, and were bred under careful observation.

2. Preparation of Splenocytes For Oral Administration

Fresh splenic tissue was obtained from syngeneic (same species, same strain) or allogeneic (same species, different strain) animals shortly prior to oral administration. Single cell splenocyte suspensions were prepared by mashing the fresh spleen through a standard stainless steel mesh (2 inches by 2 inches). Red blood cells were specifically lysed with Tris-ammonium chloride buffer according to standard proecudres well known in the art, washed twice with Hank's Balanced Salt Solution (HBSS) and resuspended into various concentrations as described below before use.

3. Preparation of Splenocyte Lysate

Splenocytes prepared as in the above method were lysed by repetitive freeze-thawing in the following manner:

(a) Cells were quick frozen at −70° C. for 30 minutes;

(b) Quick frozen splenocytes were then thawed at 37° C.;

(c) This freeze-thaw cycle was repeated one more time. The resulting materials were used for oral administration.

EXAMPLE 2: ORAL ADMINISTRATION OF PREPARED SPLENOCYTE SUSPENSION

A one milliter dose of the cell suspension as prepared in Example 1, was orally introduced to each test rat with a syringe having a ball-tipped feeding needle (Thomas Scientific, Swedesboro, N.J.).

The following laboratory immunological and pathological procedures were conducted on the lymphatic organs of the test rats.

EXAMPLE 3: MIXED LYMPHOCYTE REACTION

Cervical lymph nodes were taken from the responder (LEW) and the stimulator (WF or BN) rats. The excised nodes were then pressed through stainless steel mesh as above and suspended in Phosphate Buffered Saline.

The isolated lymph node cells were then washed twice and resuspended into RPMI 1640 medium, containing 10% fetal calf serum (FCS), 1% penicillin and streptomycin (Microbiological Associates, Walkersville, Mass.) $2\times10^{-5}$M 2-mercaptoethanol, and 5 mM HEPES, at a concentration of $6\times10^6$ cells/ml. Responder cells were seeded into a 96-well flat-bottomed culture plates (Costar Cambridge, Mass.) at 50 microliters per well, with or without irradiated stimulator cells (3000 Rads gamma irradiated using a Shepherd irradiator, Model 143-45 and a Cesium-137 source) of the same volume.

The treated cells were then cultured at 37° C. with 5% $CO_2$ for four days before they were pulsed for 6 hours with $^3$H-thymidine (1 microCi/well, obtained from NEN Dupont, Boston, Mass.). Cell proliferation was monitored by incorporation of $^3$H-thymidine measured by a Beckman liquid scintillation counter.

SUPPRESSOR ASSAY

Obtained lymph node cells were irradiated (1000 Rads of gamma radiation) and added to a test MLR at concentrations varying from 5 to 20% of total cells per well (experimental wells). Control wells were set up with no modulators while background wells had only responder cells. These cultures were incubated at 37° C. and in 5% $CO_2$ for 96 hours. Proliferation was assayed by pulsing the plates with 1 microCi/well $^3$H-thymidine for the last 6 hours of culture. The plates were then harvested as described above.

DELAYED TYPE HYPERSENSITIVITY DTH REACTIONS

Rats of each group were immunized subcutaneously in the footpad with 10 million gamma irradiated (3000 RAD) allogeneic splenocytes. Ten days later, they were injected again with the same dosage in the ear lobe. The responses were determined as the changes in the ear thickness before and 48 hours after the challenge.

CELL TYPING

The phenotypes of the extracted lymphocytes were tested by indirect immunofluorescent staining and with a fluorescence-activated cell sorter (FACS). The lymph cells were first incubated for 1 hour with primary monoclonal antibodies against the cell surface markers CD4 or CD8, or mouse immunoglobulin (Organon-Teknica, Westchester, Pa.) and washed twice with PBS containing 0.02% sodium azide. They were then further incubated with FITC-conjugated goat-anti-mouse IgG (1:40) (Organon Teknica) in the dark for 30 minutes and in the presence of 15% autologous normal rat serum. The cells were thoroughly washed and fixed with 1% formaldehyde before testing.

Additionally, surgical transplant methods of the type described in the following example were performed.

EXAMPLE 4: CARDIAC ALLOGRAFT

LEW rats were subjected to surgical transplant procedures. An accelerated rejection model was used wherein LEW strain rats were pre-sensitized with BN strain full-thickness skin grafts seven days before the cardiac allograft, with and without oral ingestion of splenocyte preparations.

Seven days later, a (LEWxBN)F1 strain test vascularized cardiac allograft was performed on each pre-treated rat. The cardiac grafts were anastomosed to the infra-renal abdominal aorta. Rejection was defined as complete cessation of heart beat as determined by daily palpation of the recipient's flank.

The above-described methods were used to obtain the following results:

I. SUPPRESSION OF THE MIXED LYMPHOCYTE REACTION (MLR) BY ORAL ADMINISTRATION OF ALLOGENEIC SPLENOCYTE PREPARATIONS

Splenocytes from WF rats were freshly prepared and were administered orally to LEW rats two, five or ten times over a 1–2 week period.

The individual dosages were 50 million cells per oral administration.

Seven days following the last oral administration, lymph nodes were taken from both a control group and those given oral splenocytes for MLR studies using WF or BN stimulators. As shown in FIG. 1, LEW rats which had ingested allogeneic splenocytes showed significantly reduced reaction against the lymphocytes from the WF strain. This phenomenon was observed in all three feeding protocols (i.e., 2, 5 or 10 times). However, only the group that received ten feedings showed suppression against the BN strain, the third party control.

These results indicate that limited ingestion of allogeneic splenocyte preparations induced antigen specific suppression of the MLR.

II. COMPARISON OF SUPPRESSION OF MLR BY ORAL ADMINISTRATION OF ALLOGENEIC VERSUS SYNGENEIC SPLENOCYTE PREPARATIONS

A dose response study was subsequently conducted to determine the effect of feeding syngeneic versus allogeneic cells. LEW rats were fed twice with 1, 5, 25 or 50 million splenocytes from either LEW or WF strains. The results are set forth in Table I below.

TABLE I

| Strains used for feeding | The Effect of Feeding Syngeneic and Allogeneic Splenocytes on MLR | | |
|---|---|---|---|
| | Dosage cells/feeding | MLR delta/CPM | Relative Response (%) |
| | — | 115015 ± 7707 | 100 |
| LEW | $1 \times 10^6$ | 128520 ± 8338 | 112 |
| | $5 \times 10^6$ | 54391 ± 10988 | 47 |
| | $25 \times 10^6$ | 39088 ± 7294 | 34 |
| | $50 \times 10^6$ | 81329 ± 8013 | 71 |
| WF | $1 \times 10^6$ | 71135 ± 13721 | 62 |
| | $5 \times 10^6$ | 79011 ± 14119 | 68 |
| | $25 \times 10^6$ | 56196 ± 15254 | 49 |
| | $50 \times 10^6$ | 73541 ± 11636 | 64 |

Feeding at the lowest dosage (1 million) of syngeneic cells did not induce suppression; all other doses, both syngeneic and allogeneic cells, show some suppression to varying degrees.

III. EFFECT OF INGESTED LYSATE OF ALLOGENEIC SPLENOCYTE PREPARATIONS ON MLR

Figure 2:
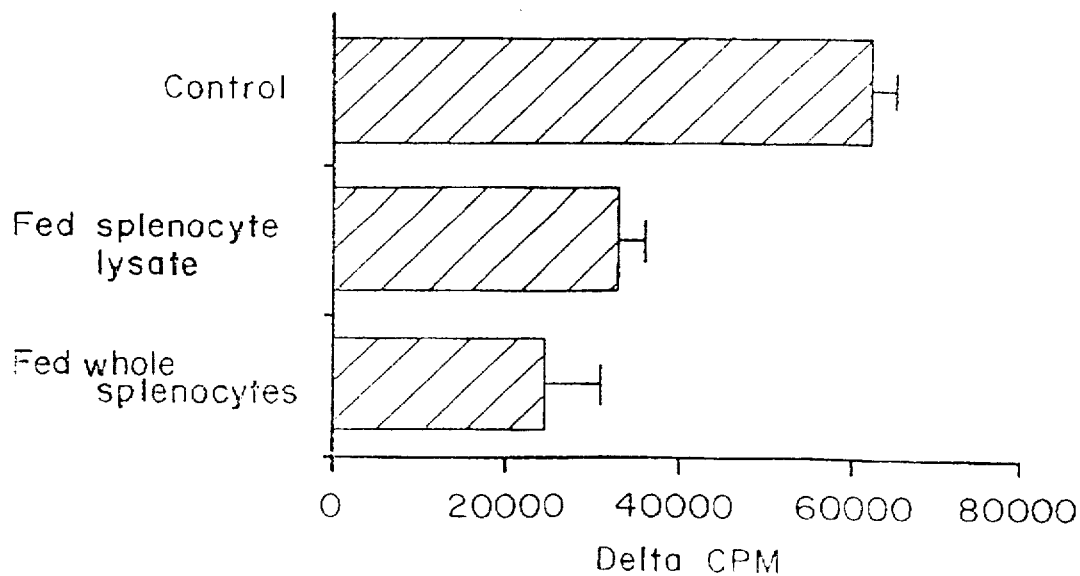
FIG. 2 is a graph showing the effect of feeding allogeneic splenocyte lysates on the mixed lymphocyte reaction.

The effect of ingested lysate alone on MLR was next studied to determine whether live splenocytes were required for the orally induced tolerance. Rats were given two separate oral doses of either live splenocytes or the corresponding lysate prepared by the repetitive freeze and thaw method (described above) and the effect of these treatments were compared. FIG. 2 shows that cell lysate alone was sufficient in suppressing the MLR, indicating that a subcellular fragment was involved in suppressing the cell-mediated immunity.

IV. KINETICS OF MLR SUPPRESSION BY ORAL ADMINISTRATION OF ALLOANTIGENS

Figure 3:
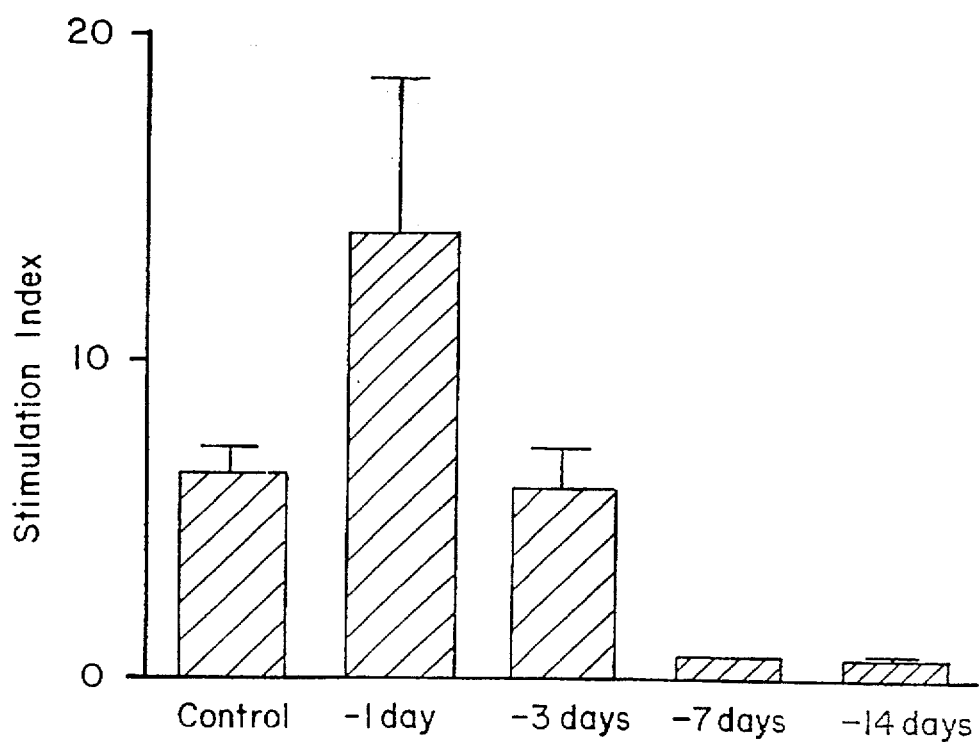
FIG. 3 is a graph showing the kinetics of oral tolerance to alloantigens.

The kinetics of the orally induced tolerance to alloantigen was studied by giving two oral doses of splenocytes to separate LEW rat groups, 14 days, 7 days, 3 days, and 1 day before the MLR was performed. As shown in FIG. 3, the groups which were given oral doses 1 day or 3 days before MLR was performed did not induce suppression. The groups with 7-day and 14-day intervals between the last oral ingestion and MLR showed dramatic reduction of proliferation in MLR, indicating that more than 4 days were required for the induction of oral unresponsiveness to alloantigens.

V. SUPPRESSION OF DTH RESPONSE AGAINST ALLOANTIGENS

Figure 4:
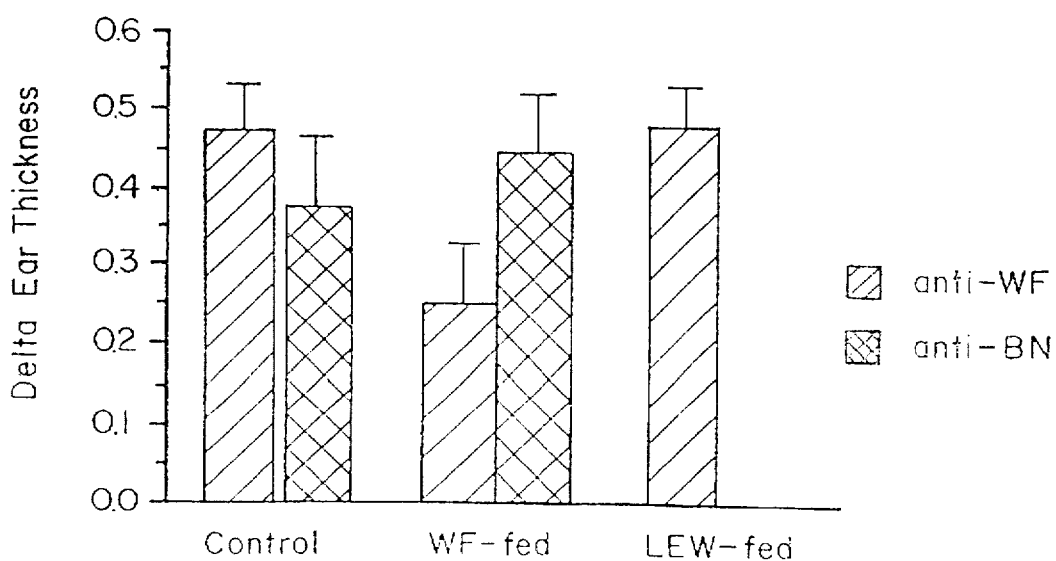
FIG. 4 is a graph depicting the effect of feeding syngeneic or allogeneic splenocytes on delayed type hypersensitivity (DTH) reactions.

In addition to the in vitro MLR, the effect of ingesting allogeneic splenocytes on the delayed type hypersensitivity (DTH) response, in vivo, in LEW rats was examined. LEW rats were orally administered 10 feedings of 50 million splenocytes from either syngeneic or allogeneic (WF) animals. After the last oral ingestion, the test for DTH was initiated with the animals being immunized subcutaneously in their foot pads. The same animals were injected again 10 days later in the ear lobes. The DTH was measured as the changes in the ear thickness before and 48 hours after the challenge. The results are shown in FIG. 4.

Approximately 50% decrease in DTH response to WF was observed in rats fed with cells of the same strain, but not in those fed with syngeneic LEW splenocytes. The DTH response against BN was not affected by the pre-treatment, indicating that the DTH suppression was antigen specific.

VI. ACTIVE SUPPRESSION IS INVOLVED IN MEDIATING DECREASED PROLIFERATION IN THE MLR

In order to study the mechanism of inhibition of MLR proliferation in the fed animals, a suppressor cell assay was performed to determine if CD8+ suppressor cells were involved in mediating the observed effects. Lymphocytes from either control or pre-fed animals were irradiated with 1000 RADS of gamma radiation before being added to a primary MLR, serving as modulators.

Lewis rats (3/group) were pre-treated 10 times orally with varying dosages (as indicated in the Table) of WF splenocytes. One week later, their cervical lymph nodes were taken and the cells served as modulator after being irradiated 1000 Rad of gamma radiation. The primary LEW anti-WF and LEW anti-BN MLR and Con-A stimulation cultures were set up as described above. Modulator cells were added to the primary cultures at a ⅕ ratio. The results are set forth in Table II below.

TABLE II

SUPPRESSION OF PRIMARY MLR BY LYMPHOCYTES FROM ALLOGENEIC SPLENOCYTES FED RATS

| | anti-WF | | anti-BN | | Con A | |
|---|---|---|---|---|---|---|
| Source of modulator | CPM ($\times 10^{-3}$) | % Supp. | CPM ($\times 10^{-3}$) | % Supp. | CPM ($\times 10^{-3}$) | % Supp. |
| — | 112 ± 21 | | 405 ± 78 | | 280 ± 4.7 | |
| control | 104 ± 11 | 7 | 464 ± 15 | 0 | 276 ± 6.6 | 1.4 |
| fed 10 × 10⁶ | 106 ± 17 | 5.3 | 334 ± 120 | 17 | 277 ± 34 | 1 |
| fed 25 × 10⁶ | 84 ± 15 | 25 | 443 ± 17 | 0 | 305 ± 3.9 | 0 |
| fed 50 × 10⁶ | 1 ± 0.9 | 99 | 84 ± 7.1 | 79 | 199 ± 12 | 29 |

The results in Table II show that adding 20% of modulators from pre-fed animals, but not from the control animals, suppressed the primary LEW-anti-WF MLR. This suggests that suppressor cells were induced after feeding and these in turn mediated suppression of the MLR.

VII. PHENOTYPE OF LYMPH NODE CELLS FROM FROM ANIMALS INGESTING SPLENOCYTES

Figure 5A:
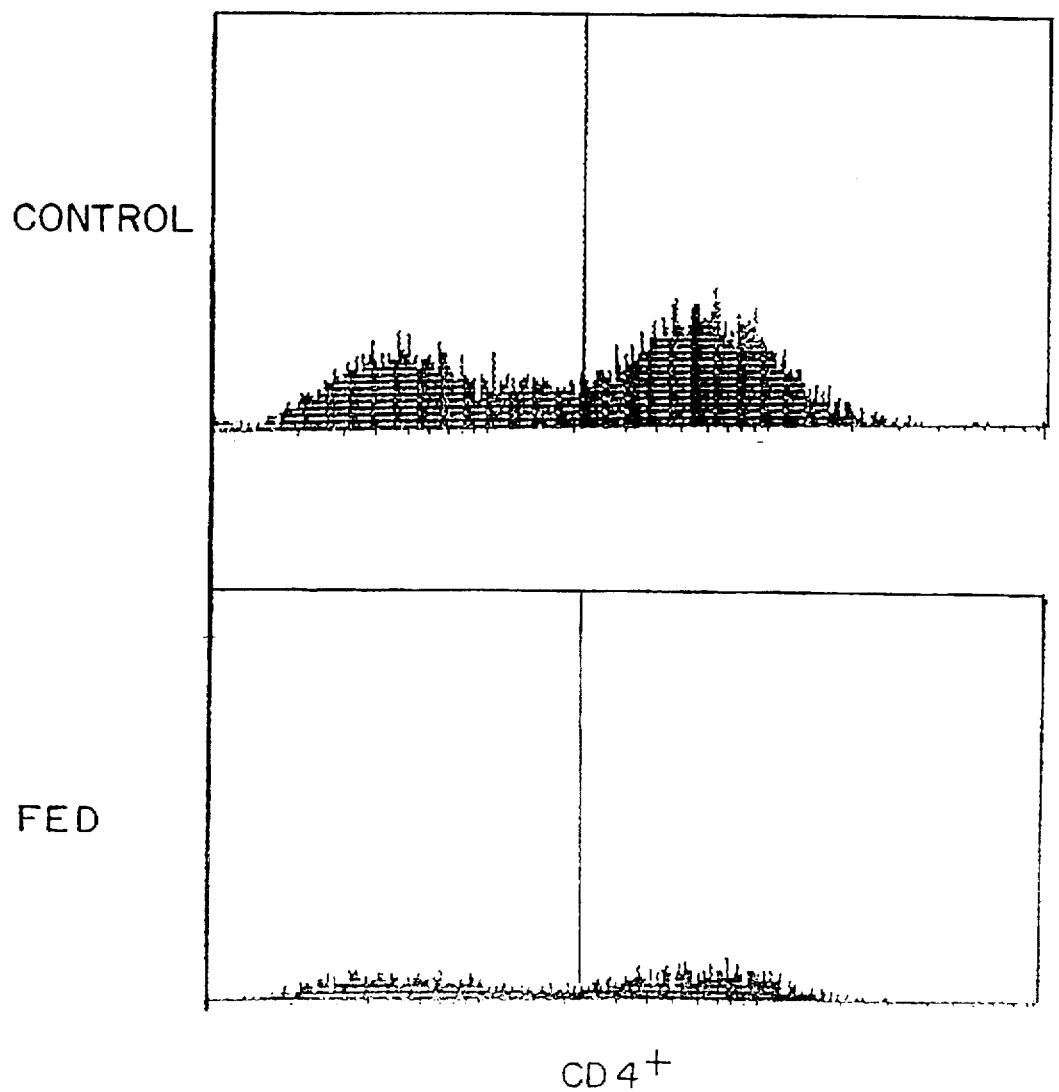
FIGS. 5A and 5B are a series of immunofluoresence analyses (histograms) showing the effect of feeding allogeneic splenocytes on lymphocyte composition.
Figure 5B:
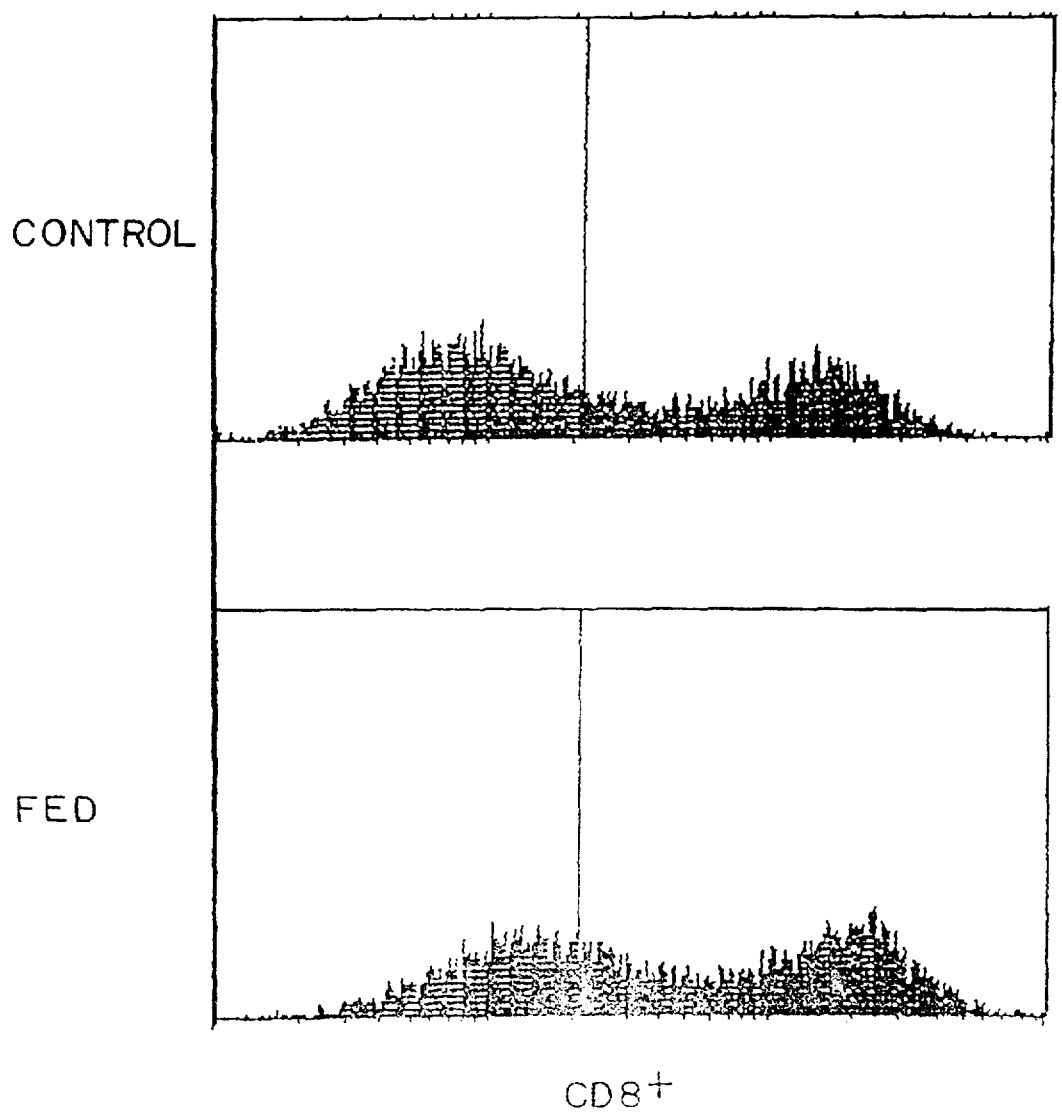

Cervical lymphocytes from either control or fed animals were cultured with irradiated WF stimulators for 5 days, then sorted for CD4+ or CD8+ cells by indirect immunofloursence staining. The results shown in FIG. 5 show that pre-feeding rats with allogeneic splenocytes resulted in an increase in CD8+ (suppressor T-cells) cells and a decrease in CD4+ (helper T-cells) cells when compared to controls.

VIII. ORAL ADMINISTRATION OF SPLENOCYTES PREVENTS ACCELERATED CARDIAC ALLOGRAFT REJECTION

To demonstrate the prevention of allograft rejection, an accelerated rejection transplantation model, as described above, was used. LEW rats were pre-sensitized with BN skin grafts 7 days before challenge with vascularized BN test cardiac allografts, to study the effects of feeding allogeneic donor splenocytes on test graft survival.

While unsensitized controls rejected their cardiac allografts on the 6th through the 8th day, all sensitized control animals hyperacutely rejected their cardiac allografts within 36 hours. Test animals fed 5–10 feedings of 50 million splenocytes, 7 days prior to the skin graft, or even on the day of the skin graft, exhibited increased test cardiac allograft survival, to 7.62±0.5 days.

These results show that feeding allogeneic splenocytes prevents sensitization and converts accelerated rejection into an acute form.

The specificity of this phenomenon was examined as described below.

Cardiac recipient LEW rats were either unfed (n=10), fed LEW (syngeneic) lymphocytes (n=8), fed BN splenocytes (but received a WF cardiac allograft, n=6) or were fed BN splenocytes (and received a BN cardiac allograft, n=8). All fed animals received 5–10 feedings of 50×10⁶ splenocytes. The results are shown in FIG. 6.

Figure 6:
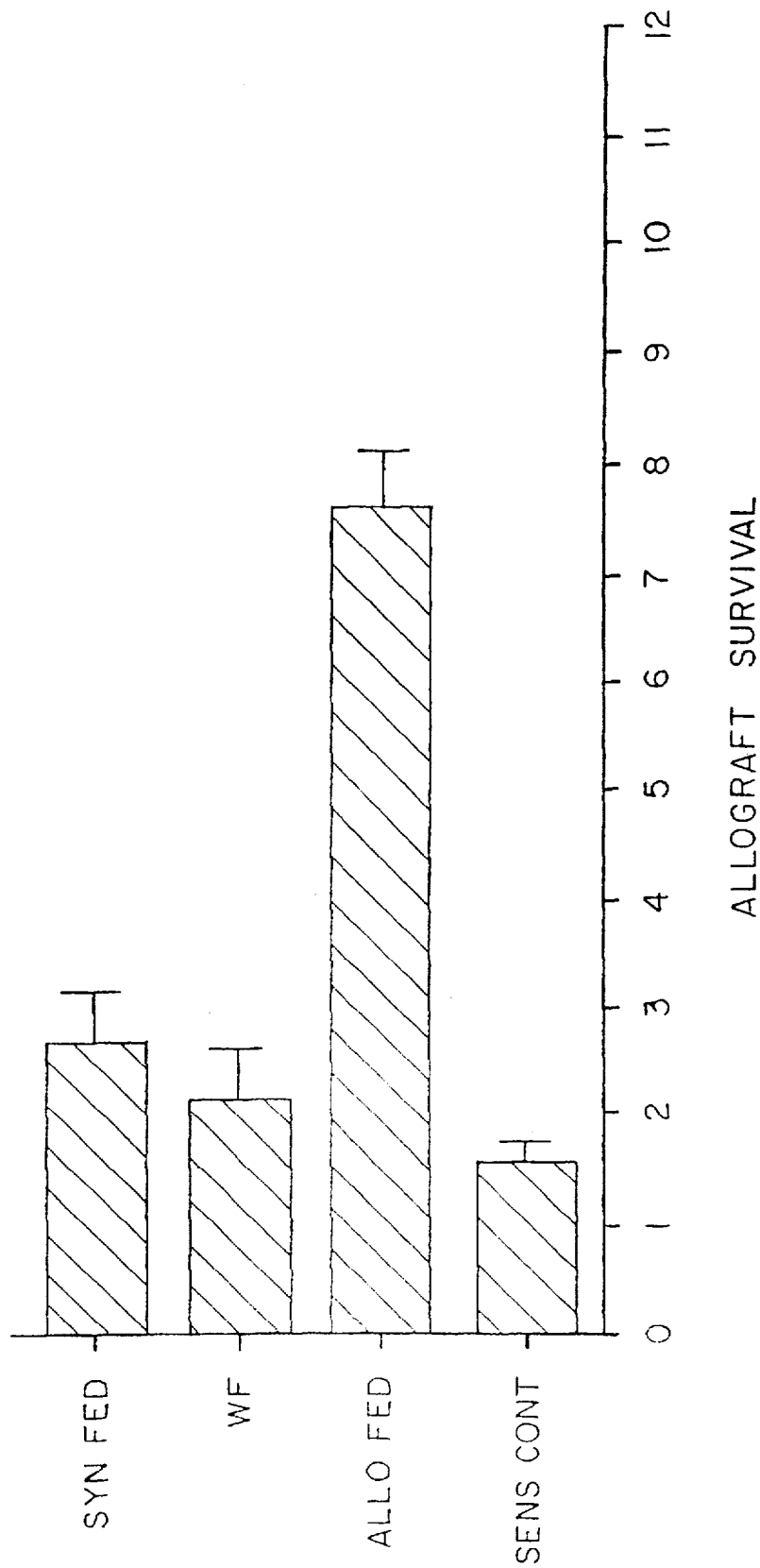
FIG. 6 is a graph showing the survival of cardiac allografts in control rats, LEW rats fed syngeneic splenocytes, LEW rats fed third party (WF) splenocytes or LEW rats fed allogeneic splenocytes.

As can be seen in FIG. 6, only the rats which were fed allogeneic splenocytes showed cardiac allograft survival beyond day 3. LEW rats fed third party (BN) lymphocytes but receiving a WF graft did not demonstrate enhanced cardiac allograft survival, demonstrating the specificity of this reaction.

In a preliminary attempt to study the mechanism of graft prolongation, the MLR of cervical lymph node cells from control and fed sensitized LEW rats were examined at 48 hours after the cardiac transplant. The results are shown in FIG. 7.

Figure 7:
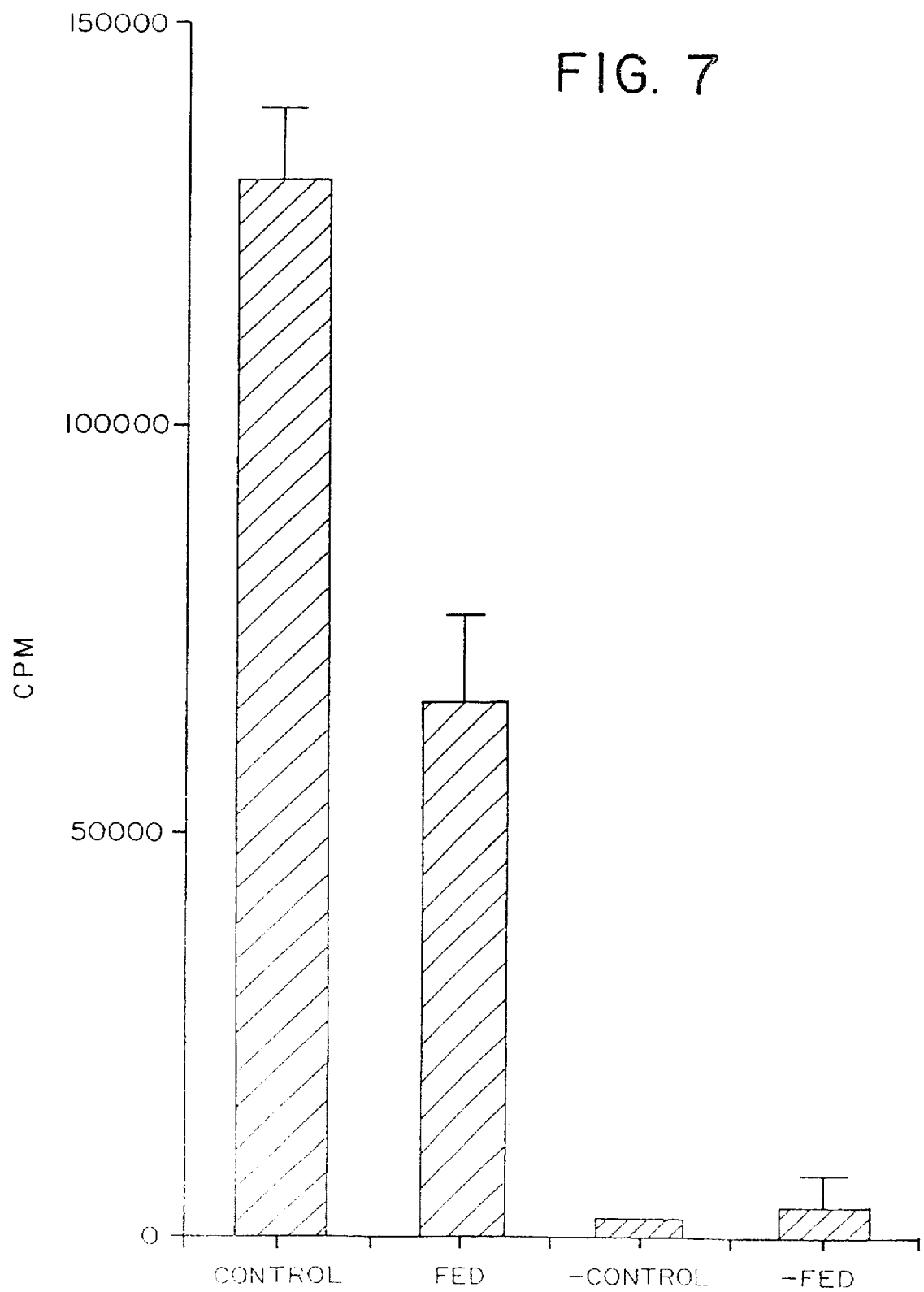
FIG. 7 is a graph showing the effects of feeding splenocytes on the MLR of skin graft recipients compared to control (non-fed) skin graft recipients.

There was a suppression of the MLR in the fed animals as compared to the control (FIG. 7). These data are consistent with the previous MLR findings in the naive animal model.

What is claimed is:

1. A method for suppressing the immune response of a recipient mammal to non-self tissue from a donor mammal comprising:

orally or enterally administering to said recipient mammal an agent in an amount effective for suppressing said immune response, said agent comprising a MHC antigen or a peptide fragment of a MHC antigen said MHC antigen being from the donor of said non-self tissue or syngeneic to the donor of said nonself tissue.

2. A method for suppressing allograft rejection in a mammal comprising orally or enterally administering to a mammal in need of such treatment an agent in an amount effective to suppress the immune response of said mammal directed against said allograft, wherein said agent comprises a MHC antigen or a peptide fragment of a MHC antigen said MHC antigen being from the donor of said allograft.

3. The method of claim 1 comprising orally or enterally administering said agent prior to the recipient mammal receiving said non-self tissue.

4. A method for suppressing the immune response of a recipient mammal to non-self tissue from a donor mammal comprising:

orally or enterally administering to said recipient mammal an agent in an amount effective for suppressing said immune response, said agent comprising a Class II MHC antigen or a peptide fragment of a Class II MHC antigen said MHC antigen being from said donor or syngeneic to said donor.

5. A method for suppressing allograft rejection in a mammal comprising orally or enterally administering to a mammal in need of such treatment an agent in an amount effective to suppress the immune response of said mammal directed against said allograft, wherein said agent comprises a Class II MHC antigen or a peptide fragment of a Class II MHC antigen said MHC antigen being from said donor or syngeneic to said donor.

6. The method of claim 4 comprising orally or enterally administering said agent prior to the recipient mammal receiving said non-self tissue.

* * * * *